(12) United States Patent
Kang et al.

(10) Patent No.: US 8,303,692 B2
(45) Date of Patent: Nov. 6, 2012

(54) SILVER NANOPARTICLE-CONTAINING POLYMER FILM FOR FACILITATED OLEFIN TRANSPORT AND METHOD FOR THE FABRICATION THEREOF

(75) Inventors: Yong-Soo Kang, Seoul (KR); Kook-Heon Char, Seoul (KR); Sang-Wook Kang, Seoul (KR)

(73) Assignee: Industry-University Cooperation Foundation Hanyang University, Seoul (KR)

( * ) Notice: Subject to any disclaimer, the term of this patent is extended or adjusted under 35 U.S.C. 154(b) by 270 days.

(21) Appl. No.: 11/610,448

(22) Filed: Dec. 13, 2006

(65) Prior Publication Data
US 2007/0256560 A1 Nov. 8, 2007

(30) Foreign Application Priority Data
Apr. 12, 2006 (KR) .................. 10-2006-0033100

(51) Int. Cl.
*B01D 53/22* (2006.01)
(52) U.S. Cl. .................. 96/14; 95/45; 96/11; 252/503; 252/514
(58) Field of Classification Search .............. 252/514, 252/503; 96/14, 11; 95/45
See application file for complete search history.

(56) References Cited

U.S. PATENT DOCUMENTS

| | | | | |
|---|---|---|---|---|
| 4,161,564 A | * | 7/1979 | Legbandt | 428/381 |
| 4,939,197 A | * | 7/1990 | Su | 524/300 |
| 5,094,797 A | * | 3/1992 | Heel et al. | 264/349 |
| 5,685,961 A | * | 11/1997 | Pourrezaei et al. | 204/192.15 |
| 6,468,331 B2 | * | 10/2002 | Kang et al. | 96/12 |
| 6,712,997 B2 | * | 3/2004 | Won et al. | 252/503 |
| 2002/0022673 A1 | * | 2/2002 | Liao et al. | 521/61 |
| 2003/0152958 A1 | * | 8/2003 | Makino et al. | 435/6 |
| 2005/0150383 A1 | | 7/2005 | Kang et al. | |

FOREIGN PATENT DOCUMENTS

| | | | |
|---|---|---|---|
| JP | 61278330 | * | 12/1986 |
| KR | 10-2005-0062641 | * | 8/2006 |
| KR | 10-0611682 | | 8/2006 |

OTHER PUBLICATIONS

Mark et al., Encyclopedia of Polymer Science & Engineering, 2nd Ed., John Wiley & Sons, vol. 12, 1985.*
Pierpont et al. "Transition Metal Complexes of o-Benzoquinone, o-Semiquinone and Catecholate Ligands," Coordination Chemistry Review, vol. 38, pp. 45-87, 1981.*
WYPYCH (Handbook of Plasticizers) ChemTee Publishing, p. 36, 2004.*
Translation of Gang et al. (KR 10-2005-0062641) Aug. 14, 2006 Nano Composite Membrane.*
Translation of Yozo (or Shigeru Tsubusaki et al.) JP 61278330 Dec. 9, 1986; some variation exists between the EPO and USPTO translations with regard to the inventors name.*

* cited by examiner

*Primary Examiner* — Jason M Greene
*Assistant Examiner* — Anthony Shumate
(74) *Attorney, Agent, or Firm* — Edwards Wildman Palmer LLP

(57) ABSTRACT

A polymer membrane, based on a facilitated transport mechanism, for separating olefins from paraffins, and a method for fabricating is provided. In the polymer membrane for facilitated transport, silver nanoparticles are partially cationized and play a role as a carrier for transporting olefins across the membrane, with p-benzoquinone serving as an electron acceptor.

3 Claims, 3 Drawing Sheets

SILVER NANOPARTICLE-CONTAINING POLYMER FILM FOR FACILITATED OLEFIN TRANSPORT AND METHOD FOR THE FABRICATION THEREOF

CROSS REFERENCE

Applicant claims foreign priority under Paris Convention and 35 U.S.C. §119 to a Korean Patent Application No. 10-2006-0033100, filed on Apr. 12, 2006 with the Korean Intellectual Property Office.

BACKGROUND OF THE INVENTION

1. Field of the Invention

The present invention relates to a polymer membrane for facilitated olefin transport and a method for fabricating the same. More particularly, the present invention relates to a polymer membrane for facilitated olefin transport, coated with positively charged silver nanoparticles, which shows excellent selectivity for olefins over paraffins and thus stably conducts the facilitated transport of olefins for a long period of time, and a method for the fabrication thereof.

2. Description of the Related Art

Polymer membranes have found applications in separation of various mixtures into individual constituents, particularly into carbon dioxide and methane, into oxygen and air, and into organic vapor and air. However, conventional polymer membranes are not sufficiently capable of separating olefins and paraffins, for example, propylene and propane, butylene and butane, and the like, because olefins and paraffins are similar in molecular weight and physical properties.

With the introduction of the concept of a facilitated transport as a solution to the problem of difficulty in separating olefins and paraffins having similar molecular weights, active research has been conducted to apply polymer membranes for separation therebetween.

Facilitated transport, also known as facilitated diffusion, is a process of diffusion, a form of passive transport, where molecules diffuse across membranes, with the assistance of transport molecules, called carriers, which are solute specific. In contrast to active transport, facilitated transport does not require energy, and carries molecules or ions down a concentration gradient. A polymer membrane for facilitated transport has thereon a carrier which can reversibly react with specific molecules of a mixture in order to separate them. Across a facilitated transport membrane, thus, a specific molecule (for example, an olefin molecule) not only diffuses due to a concentration gradient, based on Fick's law, but also is transported by the carrier specific thereto with an increase in selectivity and transmittance.

For facilitated transport, solid or liquid membranes on which a silver salt, for example, $AgBF_4$ or $AgCF_3SO_3$, is supported as a carrier, have been suggested. An initial model of the Ag-bound membranes suffers from the disadvantage of a decrease in the activity of the silver salt bound thereto with an increasing usage time period. Phthalate compounds or surfactants have been suggested in order to prevent the silver salt from decreasing in activity.

However, silver salts in combination with conventional surfactants, such as phthalate compounds, need an additional humidifying process and cannot maintain selectivity for olefins over paraffins for a long period of time.

Therefore, there is a need for a novel transport system that not only exhibits high selectivity for olefins, but also maintains the facilitated transport performance at a high rate for a long period of time.

Exhibiting characteristic physicochemical properties in various fields, including surface-enhanced Raman-scattering, catalysis, photonics, and sensors, silver nanoparticles have lately attracted considerable attention. The characteristic physicochemical properties of silver nanoparticles, different from those of silver or silver salts, are attributed to the greater reactivity based on the larger surface area of nanoparticles.

For example, an experiment for the reaction of silver nanoparticles with oxygen molecules at low temperature demonstrated that smaller nanoparticles exhibit higher ability to decompose oxygen molecules into atoms. On the other hand, when reacted with bulk nanoparticles, oxygen molecules are for the most part decomposed into $O_2^{-5}$. Silver nanoclusters in an aqueous solution are known to have the ability to transport electrons to suitable acceptors and take partial positive charges if the circumstances permit, thereby showing superior chemical activity.

SUMMARY OF THE INVENTION

Leading to the present invention, intensive and thorough research into a polymer membrane for facilitated olefin transport, conducted by the present inventors, resulted in the finding that silver in the form of nanoparticles rather than salts exhibits sufficiently potent physicochemical activity to be positively charged in the presence of a suitable electron acceptor, thereby being able to play an important role in the facilitated transport of olefins across a polymer membrane.

Therefore, it is an object of the present invention to provide a polymer membrane for facilitated olefin transport by way of silver nanoparticles.

It is another object of the present invention to provide a method for fabricating the polymer membrane.

In accordance with an aspect, the above object is accomplished by providing a polymer membrane for facilitated olefin transport, comprising a polymer, silver nanoparticles, and p-benzoquinone.

In a preferable modification, the polymer, the silver nanoparticles and the p-benzoquinone are used in a weight ratio of 1:1:0.5~0.85.

It is preferable that the silver nanoparticles be 100 nm or less in mean particle size.

The polymer is preferably EPR (poly(ethylene-co-propylene)).

Particularly, the polymer membrane further comprises a porous support.

In accordance with another aspect, provided is a method for fabricating a polymer membrane, comprising: dissolving a polymer in a solvent to give a polymer solution; suspending silver nanoparticles and p-benzoquinone in the polymer solution to give a suspension; coating a support with the suspension; evaporating the solvent from the support coated with the suspension at room temperature in a nitrogen atmosphere; and drying the polymer coating to completion at room temperature in a vacuum.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
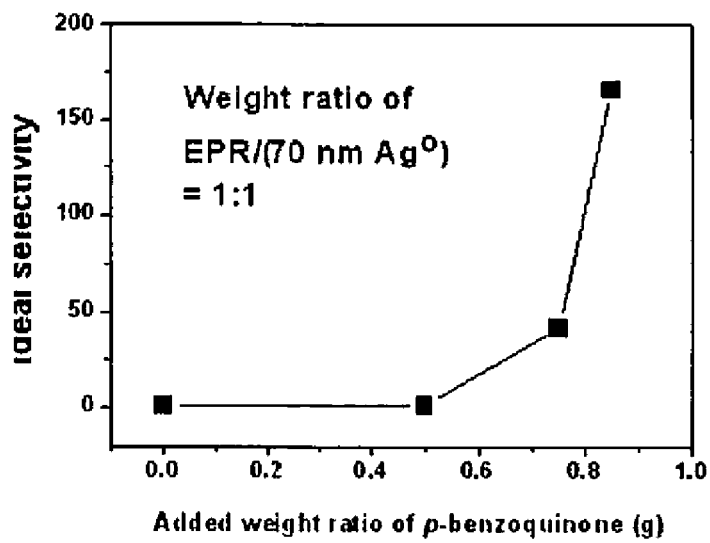
FIG. 1 is a graph showing ideal selectivities for propylene/propane of the polymer membranes prepared in Comparative Example and Examples 1 o 3.

Below, a detailed description will be given of the present invention.

A conventional metal salt-containing polymer membrane for facilitated olefin transport is based on a mechanism in which the metal salt on the polymer membrane is dissociated into a metal cation and a salt anion, the metal cation reversibly reacting with the double bonds of olefinic hydrocarbons to form complexes which can directly participate in facilitated transport. Thus, conventional metal salt-containing polymer membranes for facilitated olefin transport require solvents for dissociating the metal salt into its constituent ions. For example, water is used as a solvent to dissociate metal salt into a metal cation and a salt anion.

Likewise, silver nanoparticles, which serve as carriers in the polymer membrane of the present invention, are required to be cationized for facilitated olefin transport. In this regard, the present invention features the use of p-benzoquinone as a solvent for cationizing silver nanoparticles.

Considering photosynthesis, in which p-benzoquinone, serving as an electron acceptor, is reduced to hydroquinone, silver nanoparticles can be partially positively charged in the presence of p-benzoquinone and thus play a role as a carrier for facilitated olefin transport.

The technical feature of the present invention resides in the use of silver nanoparticles and p-benzoquinone in the preparation of polymer membranes for facilitated olefin transport, irrespective of type of the polymer used. Therefore, the present invention is not limited to the following examples, in which predetermined concentrations of specific polymers are employed, but is applicable to all conventional polymer membranes.

A better understanding of the present invention may be achieved through the following examples, which are set forth to illustrate, but are not to be construed to limit the present invention.

Example 1

Silver nanoparticles (mean particle size 70 nm, purity 99.5%), p-benzoquinone and poly(ethylene-co-propylene) (EPR, Mw=$1.7 \times 10^5$ g/mol) were purchased from Aldrich Chemical and used without further processing.

The preparation of an EPR/Ag°/p-benzoquinone membrane started with a toluene solution containing 10 wt. % of EPR. In this solution were suspended silver nanoparticles and p-benzoquinone in such amounts as to form a weight ratio of EPR:silver particle:p-benzoquinone 1:1:0.5. Herein, Ag° stands for silver particles.

A microporous polysulfone support (Saehan Industries) was coated with the polymer solution using an RK Control Coater (Model 101, Control Coater RK Print-Coat Instruments LTD).

The coated support was dried at room temperature in a convection oven filled with a nitrogen gas to evaporate toluene, and finally dried at room temperature in a vacuum oven.

SEM data showed that the polymer membrane had a coating about 1 μm thick.

Example 2

A polymer membrane was prepared in the same manner as in Example 1, with the exception that the weight ratio of EPR:Ag nanoparticle:p-benzoquinone was set at 1:1:0.75. The coating was measured to be about 1 μm.

Example 3

A polymer membrane was prepared in the same manner as in Example 1, with the exception that the weight ratio of EPR:Ag particle:p-benzoquinone was set at 1:1:0.85. The coating was measured to be about 1 μm.

Comparative Example

A polymer membrane was prepared in the same manner as in Example 1, with the exception that no silver particles were used. The coating was measured to be about 1 μm.

The weight ratios of components used for the coatings of Examples 1 to 3 and Comparative Example are summarized in Table 1, below.

TABLE 1

| | (weight ratio) | | |
|---|---|---|---|
| | EPR | Ag° | p-benzoquinone |
| Ex. 1 | 1 | 1 | 0.50 |
| Ex. 2 | 1 | 1 | 0.75 |
| Ex. 3 | 1 | 1 | 0.85 |
| Comparative. Ex. | 1 | 1 | none |

The weight ratio of silver nanoparticles to p-benzoquinone is not limited to the above-set may vary with the kind of the polymer used. When the polymer and the silver nanoparticles are set at a weight ratio of 1:1, the content of p-benzoquinone preferably ranges within a weight ratio from 0.5 to 0.85 relative to the weight of the silver nanoparticles. For example, if the weight ratio of p-benzoquinone to silver nanoparticles is less than 0.5, the silver nanoparticles cannot be sufficiently activated. On the other hand, a weight ratio exceeding 0.85 would cause phase separation (refer to data of Experimental Example 2).

Experimental Example 1

Assay for Permeability to Propylene and Propane

Propylene and propane gases, which are similar in molecular weight and representative of olefins and paraffins, were used to test the gas permeability of the polymer membranes prepared in Examples above. Gas permeance through the polymer membranes prepared in the above examples is shown for individual gases of propylene and propane in FIGS. 1 and 2 and for a mixed gas of propylene and propane in FIGS. 3 and 4.

A permeability assay was conducted using a mass flow meter (MFM). The gas permeance of a given polymer membrane is expressed in units of GPU wherein 1 GPU=1×10$^{-6}$ cm$^3$(STP)/(cm$^2$ sec cmHg). As for a mixture gas of propylene and propane, MEM alone cannot measure the gas permeance of the membrane to individual components. In this regard, gas chromatography was also used in combination with MEM to measure the polymer membrane for gas permeability to the propylene and propane in mixture. For this, a gas chromatograph equipped with a TCD detector and a unibead 2S 60/80 packed column (G1530A, Hewlett-Packard) was used.

First, the polymer membrane was measured for permeance to individual gases of the propylene and propane mixture. Based on the measurements, ideal selectivity was calculated according to the following formula:

$$\text{Ideal Selectivity} = \frac{\text{Permeability to Propylene}}{\text{Permeability to Propane}}$$

Figure 2:
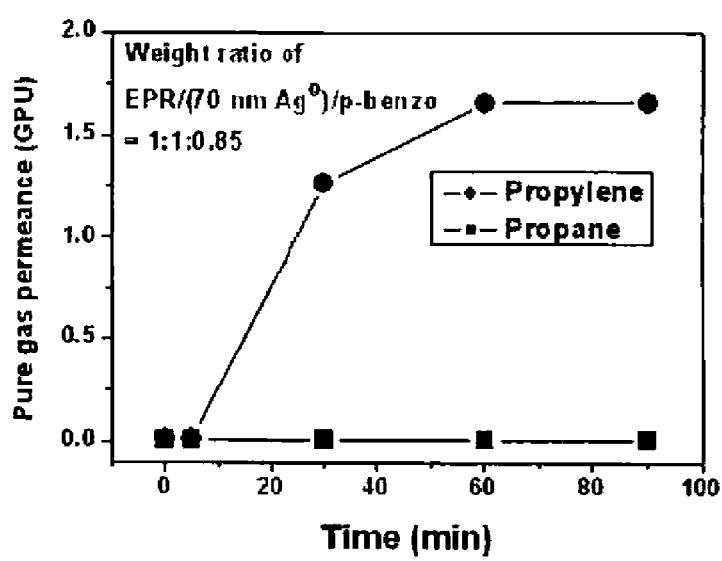
FIG. 2 is a graph showing the pure gas permeance of propylene and propane through the polymer membrane of Example 3 over time.

Data on the ideal selectivity and the permeance to individual gases are given in FIGS. 1 and 2.

FIG. 1 depicts the ideal selectivity for propylene to propane plotted against the content of p-benzoquinone. The EPR/silver nanoparticle membrane devoid of p-benzoquinone was measured to have a gas permeance of 0.01 GPU with ideal selectivity approximate to 1, indicating that the membrane was almost useless for the separation of propylene from propane.

In contrast, the ideal selectivity for propylene to propane of the polymer membrane according to the present invention increases with an increase in the content of p-benzoquinone, as shown by the polymer membranes prepared in Examples 1 to 3. When the weight ratio of p-benzoquinone to silver nanoparticles increased to 0.85 (Example 3), the ideal selectivity was as high as 165. Particularly from a weight ratio of 0.75 of p-benzoquinone to silver nanoparticles (Example 2), the ideal selectivity was found to sharply increase. These data imply that the silver nanoparticles in the polymer membrane are required to be cationized sufficiently to play a role as carriers suitable for facilitated transport.

FIG. 2 depicts propylene and propane permeance through the polymer membrane of Example 3 (weight ratio of p-benzoquinone 0.85) plotted against time. As seen in these plots, the propylene permeance increases 30 min after the initiation of the experiment and reaches a steady state 1 hour after the initiation of the experiment. In contrast, propane permeance remained low throughout the experiment. Taken together, the data obtained in FIGS. 1 and 2 demonstrate that p-benzoquinone allows the silver nanoparticles to take on the surfaces thereof positive charges necessary for facilitated olefin transport.

Figure 3:
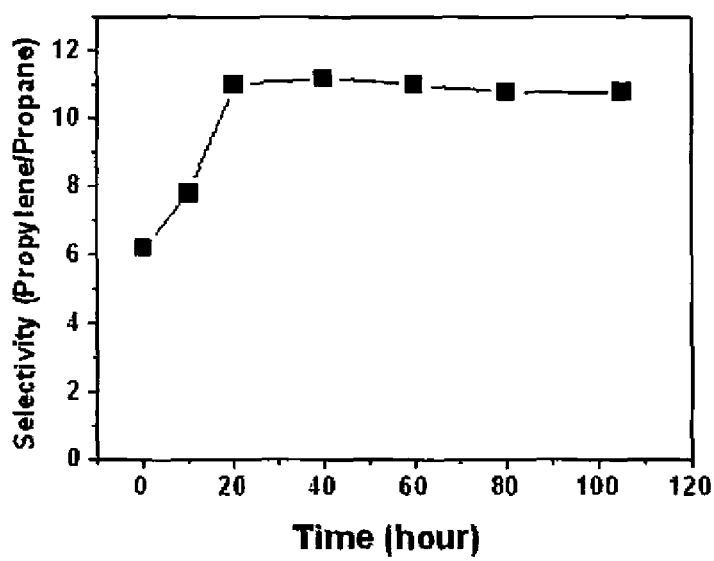
FIG. 3 is a graph showing the selectivity for propylene of the polymer membrane of Example 3 over propane over time.
Figure 4:
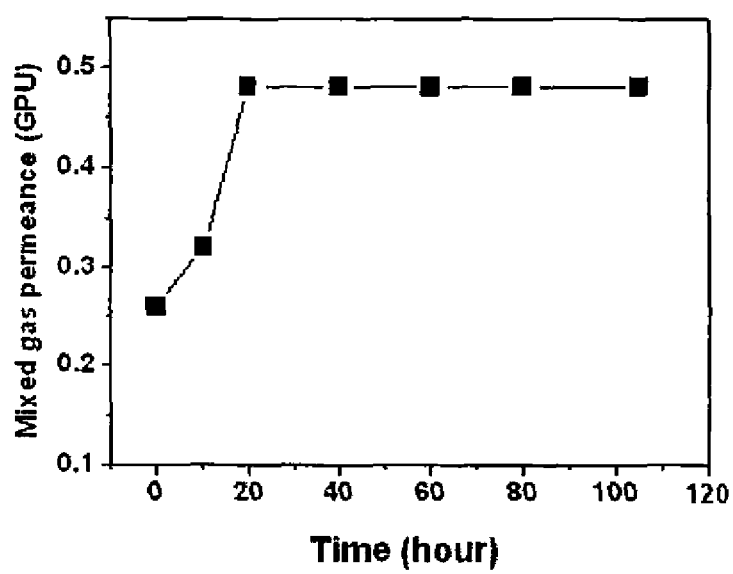
FIG. 4 is a graph showing the permeance of a propylene/propane mixed gas through the polymer membrane of Example 3 over time.

With reference to FIGS. 3 and 4, the selectivity of the polymer membrane of the present invention for propylene to propane and the permeance of propylene and propane through the membrane are shown, respectively.

The polymer membrane of the present invention was assayed for separation stability with regard to propylene/propane mixed gas. It was measured for permeability to propylene/propane mixed gas for 105 hours. As shown in FIGS. 3 and 4, the selectivity and the gas permeance were maintained almost constant over time throughout the experiments. From these data, it can be found that the silver nanoparticles positively charged by p-benzoquinone within the polymer membrane play a stable role as an olefin carrier.

Taken together, the results of FIGS. 1 to 4 demonstrate that the silver nanoparticles activated, that is, positively charged by p-benzoquinone, could reversibly react with the π bond of olefin, allowing the polymer membrane of the present invention to perform the facilitated transport of olefins.

Experimental Example 2

XPS Assay

Pure silver and the silver materials used in Comparative Example and Examples 1 and 2 were measured for binding energy through X-ray Photoelectron Spectroscopy (hereinafter referred to as XPS) to confirm that the carrier activity of silver nanoparticles increased with (the number of) positive charges taken on the surface thereof. The results are given in FIG. 5.

For X-ray Photoelectron Spectroscopy (XPS), a Physical Electronics PHI 5400 X-ray photoelectron spectrometer, manufactured by Perkin-Elmer, was used.

Figure 5:
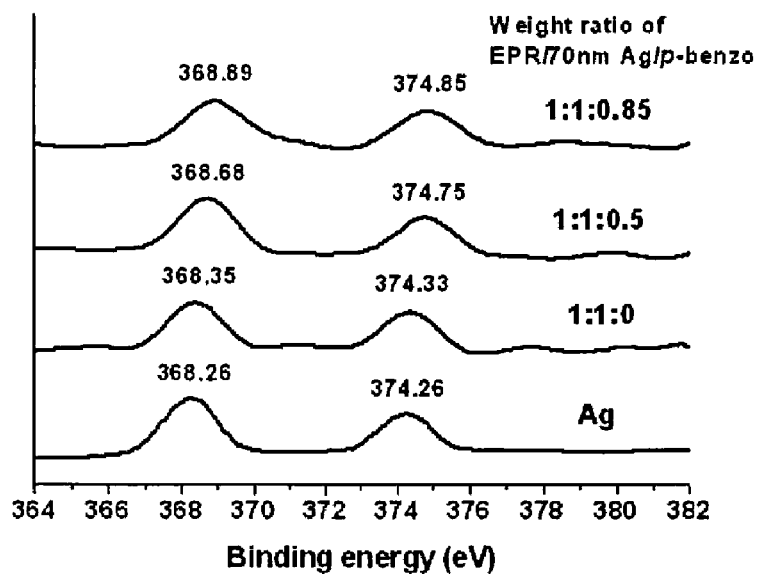
FIG. 5 provides XPS (X-ray photoelectron spectroscopy) spectra showing the binding energies of pure silver and silver materials used in the polymer membranes of Comparative Example and Examples 1 and 3.

As shown in FIG. 5, the binding energy of the d$_{5/2}$ orbital of silver increases from 368.26 to 368.89 an increase in the content of p-benzoquinone in EPR/Ag° systems, indicating that the valence electrons of silver increase in binding energy as a result of the interaction between silver and p-benzoquinone.

Although not shown, the binding energy was decreased when the weight ratio of p-benzoquinone to nanosilver particles exceeds 0.85:1. This is believed to result from the aggregation, rather than uniform distribution, of p-benzoquinone when it is used excessively. It is obvious that the critical value for the content of p-benzoquinone varies depending on the kind of polymer membrane used. It is preferred that the weight ratio of p-benzoquinone to silver nanoparticles be set at 0.85 or less:1 in the polymer membrane having a weight ratio of EPR/Ag° 1:1.

Figure 6:
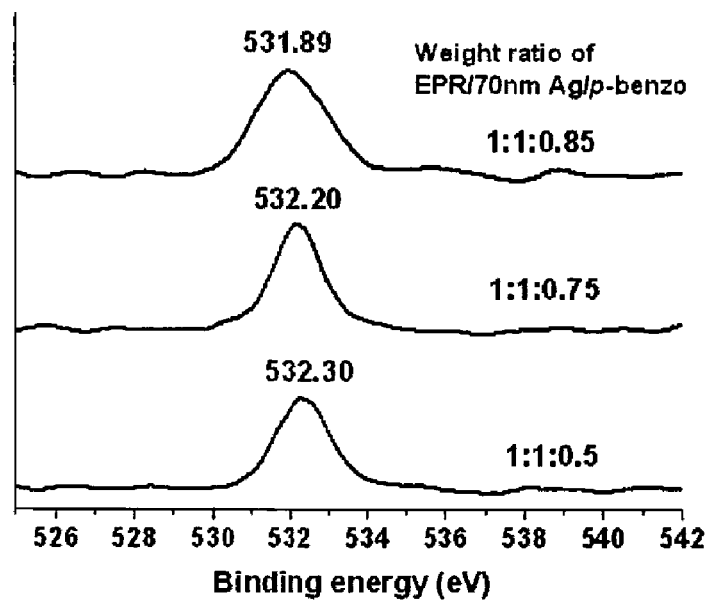
FIG. 6 provides XPS spectra showing the binding energies of oxygen of p-benzoquinone in the polymer membranes prepared in Examples 1 to 3.

In addition, the polymer membranes of Examples 1 to 3 were subjected to XPS to monitor the change of p-benzoquinone in binding energy to oxygen in the EPR/Ag° systems, and the results thereof are given in FIG. 6. As seen in FIG. 6, the binding energy to oxygen of p-benzoquinone gradually increases from 532.30 eV (Example 1) to 531.89 eV (Example 3) as the content of p-benzoquinone increases.

Taken together, the data obtained in FIGS. 5 and 6 imply that an increase in the content of p-benzoquinone in an EPR/Ag° system decreases the polarity of oxygen of p-benzoquinone, leading to a positive interaction between olefin and silver nanoparticles, which makes it possible to conduct facilitated transport.

Although only EPR is used as a polymer in the preferred embodiments of the present invention, they have been disclosed for illustrative purposes. Featuring the use of silver nanoparticles as carriers for facilitated transport and p-benzoquinone as an activator for silver nanoparticles in a polymer membrane, the present invention is not limited to the polymer. Accordingly, it should be understood that all polymer membranes for facilitated transport, as long as they have thereon silver nanoparticles positively charged by p-benzoquinone, fall within the scope and spirit of the invention.

As described hitherto, the present invention provides a polymer membrane for the selective facilitated transport of olefin/paraffin using silver nanoparticles, which is advantageous over conventional polymer membranes using metal salts in that it does not require a humidification process necessary for conventional membranes and can stably separate olefins from paraffins for a long period of time.

Although the preferred embodiments of the present invention have been disclosed for illustrative purposes, those skilled in the art will appreciate that various modifications, additions and substitutions are possible. Accordingly, such modifications, additions and substitutions should be understood as falling within the scope and spirit of the invention.

What is claimed is:

1. A polymer membrane for facilitated olefin transport, comprising:
    a polymer;
    silver nanoparticles with mean particle size of 100 nm or less;
    p-benzoquinone; and
    a porous support,
    wherein a weight ratio of the polymer, the silver nanoparticles and the p-benzoquinone is from 1:1:0.5 to 1:1:0.85,
    wherein the silver nanoparticles are partially cationized by the p-benzoquinone and play a role as carriers for transporting olefins across the membrane.

2. The polymer membrane according to claim 1, wherein the polymer is EPR (poly(ethylene-co-propylene)).

3. A method for fabricating a polymer membrane, comprising:
    dissolving a polymer in a solvent to give a polymer solution;
    suspending silver nanoparticles and p-benzoquinone in the polymer solution to give a suspension;
    coating a support with the suspension;
    evaporating the solvent from the support coated with the suspension at room temperature in a nitrogen atmosphere; and
    drying the polymer coating to completion at room temperature in a vacuum,
    wherein a mean particle size of the silver nanoparticles is 100 nm or less,
    wherein a weight ratio of the polymer, the silver nanoparticles, and the p-benzoquinone is from 1:1:0.5 to 1:1:0.85.

* * * * *